United States Patent [19]

Seki et al.

[11] 4,323,576
[45] Apr. 6, 1982

[54] DERIVATIVES OF PYRAZOLE FOR USE IN THERAPY

[75] Inventors: Kunio Seki; Masahiko Ohki, both of Shiga, Japan

[73] Assignee: Morishita Pharmaceutical Co., Ltd., Osaka, Japan

[21] Appl. No.: 205,936

[22] Filed: Nov. 12, 1980

[30] Foreign Application Priority Data

Nov. 16, 1979 [JP]   Japan .................................. 54-149103

[51] Int. Cl.³ .......................................... A61K 31/415
[52] U.S. Cl. ............................................... 424/273 P
[58] Field of Search ..................... 424/273 P; 548/378

[56] References Cited

U.S. PATENT DOCUMENTS 2,931,814   4/1960   Karmas ........................... 424/273 P

FOREIGN PATENT DOCUMENTS 1048104  11/1966  United Kingdom ............ 424/273 P

*Primary Examiner*—Donald B. Moyer
*Attorney, Agent, or Firm*—Wegner & Bretschneider

[57] ABSTRACT

Derivatives of pyrazole represented by the general formula:

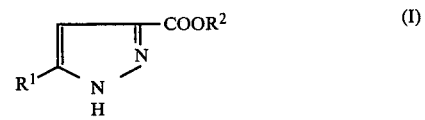

wherein $R^1$ represents an alkyl group of 7 to 11 carbon atoms and $R^2$ represents a hydrogen atom or a lower alkyl group, have therapeutic activity with a very low mammalian toxicity, and in particular can be used in the treatment of hyperlipemia.

8 Claims, 6 Drawing Figures

DERIVATIVES OF PYRAZOLE FOR USE IN THERAPY

BACKGROUND OF THE INVENTION

The present invention relates to derivatives of pyrazole for use in therapy.

Hitherto, various antihyperlipemic pharmaceutical compositions have been proposed for treatment of hyperlipemia, but, they have an important demerit of causing side effects during the long term administration to the patients. For instance, clofibrate which has hitherto been generally administered as an antihyperlipemic pharmaceutical composition causes the diseases in the bile duct system and is in danger of causing cancer, and accordingly, the clinical administration of clofibrate has been restricted. On the other hand, pharmaceutical compositions containing nicotinic acid as an active ingredient for treating hyperlipemia are rarely used because of its side effect of causing flushing or eruptions on the face and skin.

5-Methylpyrazol-3-carboxylic acid had been reported to have an activity to reduce the level of serum lipid (refer to Kupiecki, F. et al., J. pharmacol. Expt. Therap., 160 (1), 166, 1968), it was proved later that in addition to the uncertainty of the derivative's clinical effect in treatment of hyperlipemia, it showed a side effect of causing the reduction of blood sugar-level and accordingly, it was not suitable as an active ingredient in the pharmaceutical composition for treating hyperlipemia (refer to Land, P. D. et al., Arzneim. Forsch., 25 (1), 117, 1975).

The inventors of the present invention, considering the above-mentioned present situation of antilipemic agents, after synthesizing and testing various compounds, has found that the derivatives of pyrazole represented by the general formula (I) shown later have an excellent antilipemic activity in common substantially without exhibiting noticeable side effects, and has attained the present invention.

The following description is the detailed explanation of the present invention.

DETAILED DESCRIPTION OF THE INVENTION

Figure 1:
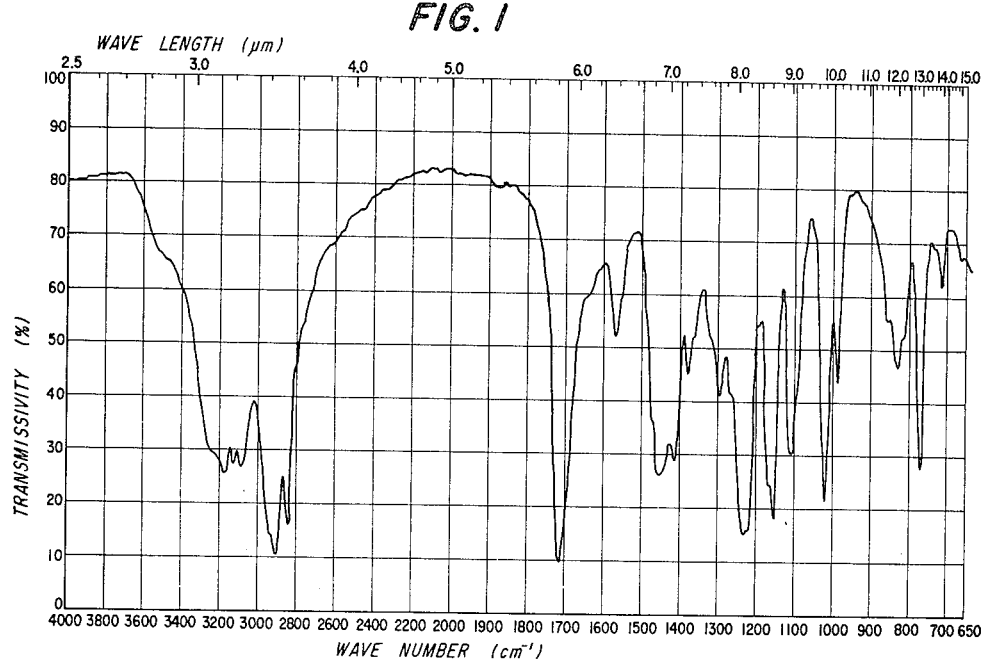
FIGS. 1 to 6 of drawing show the infrared absorption spectra of pyrazole prepared by the methods described in Examples 1 to 6, according to the present invention, the number of each figure corresponding to the number of each Example, as is seen.
Figure 2:
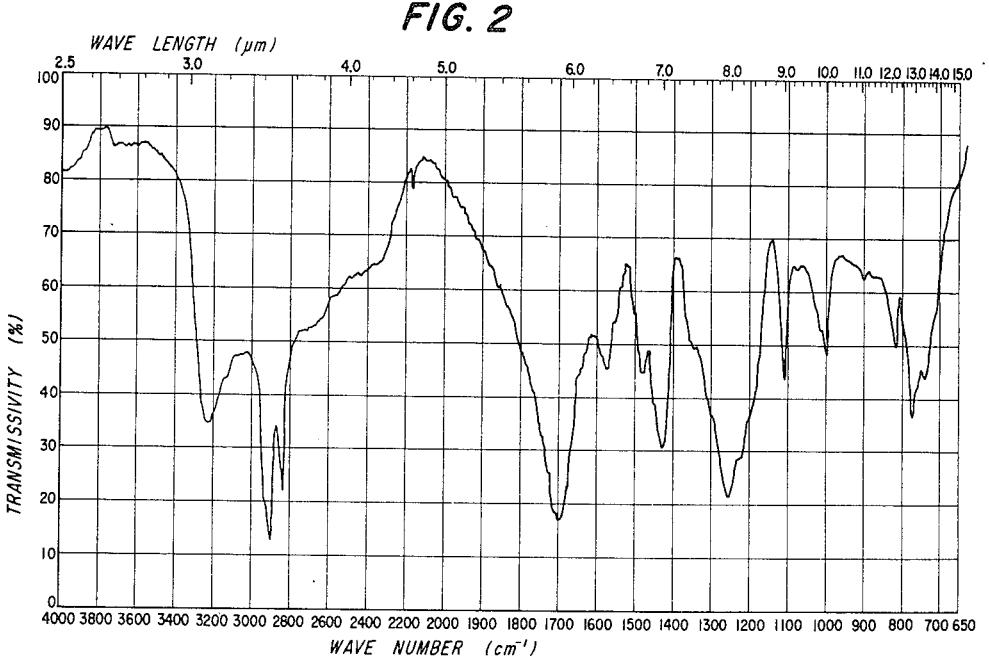
Figure 3:
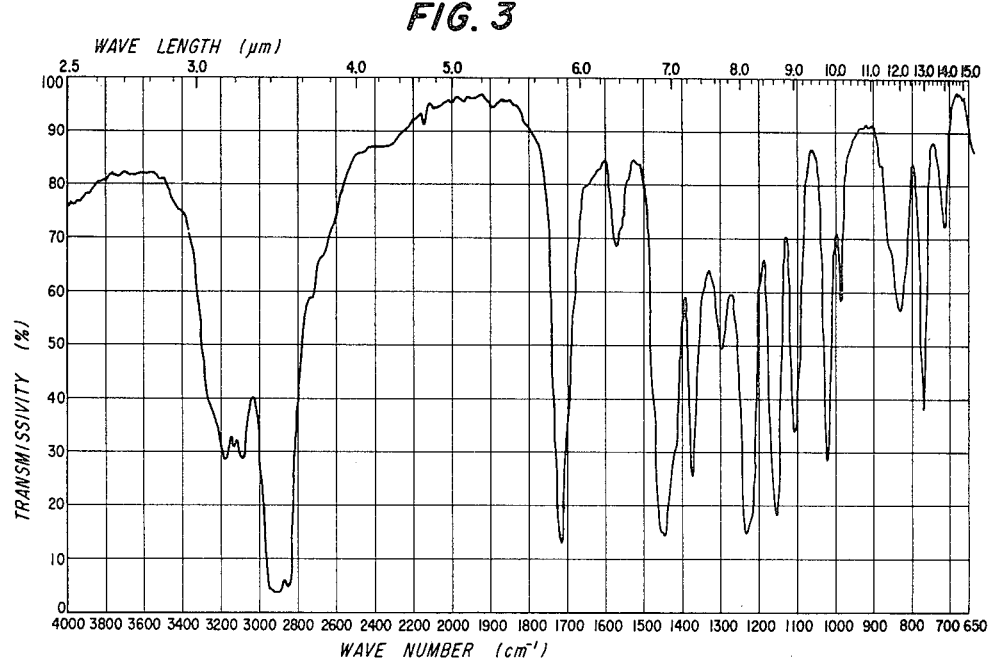
Figure 4:
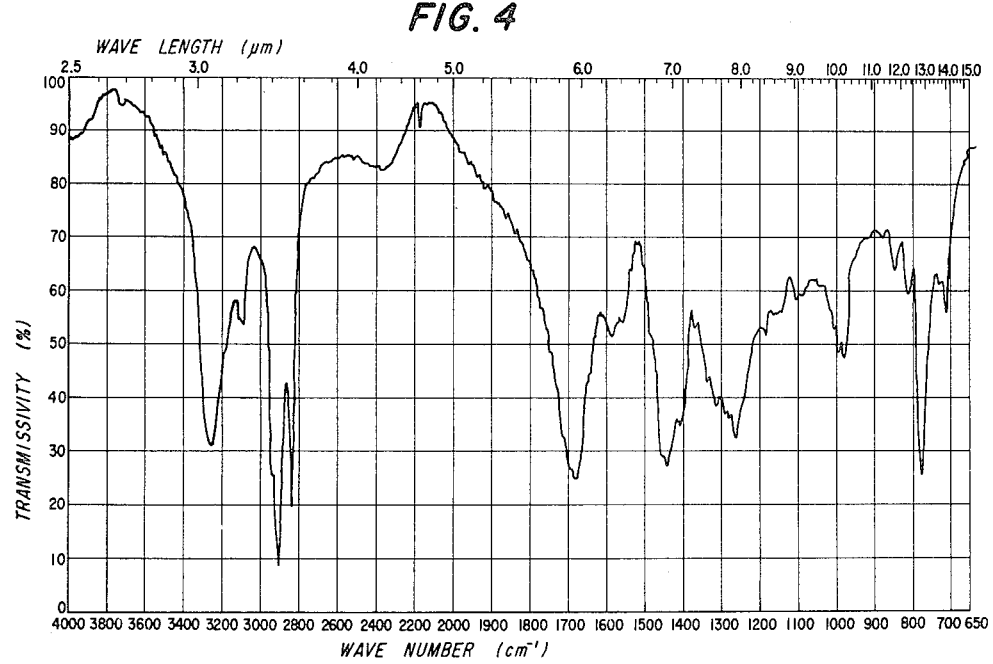
Figure 5:
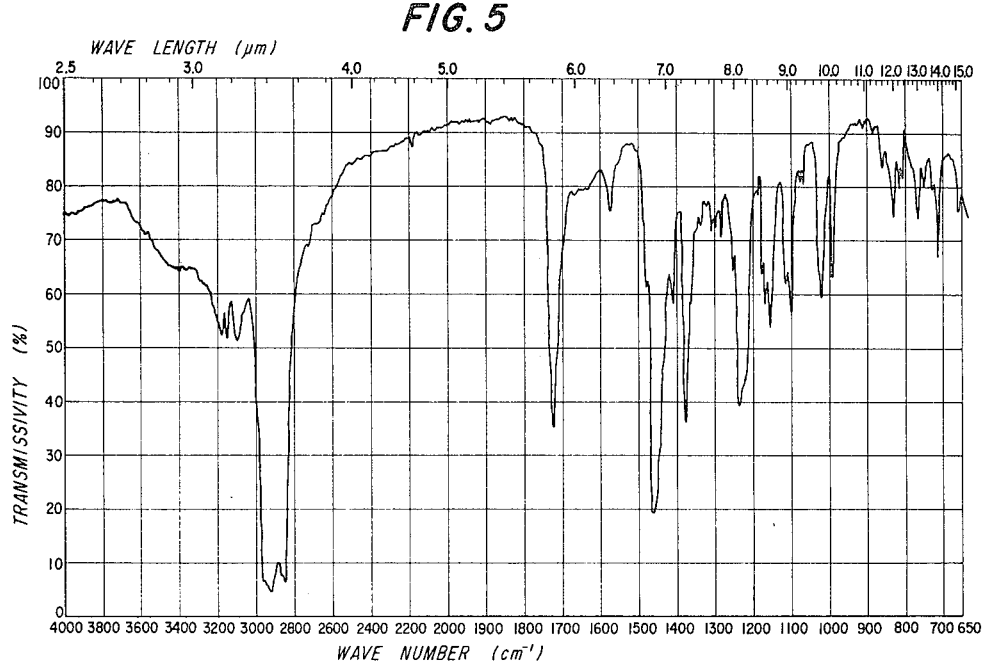
Figure 6:
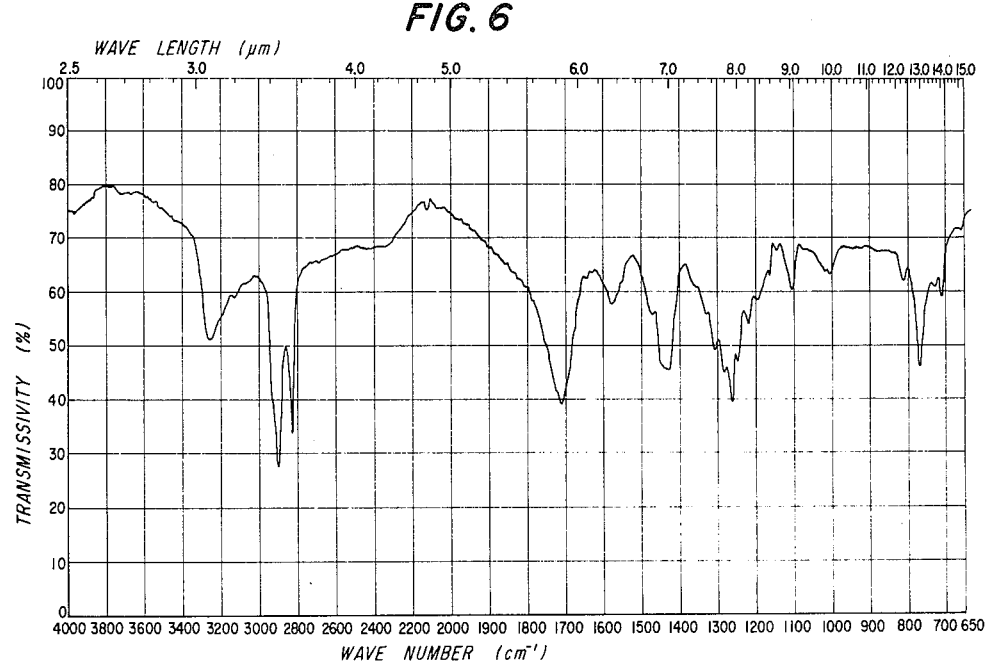

The derivatives of pyrazole of the present invention are represented by the following general formula (I)

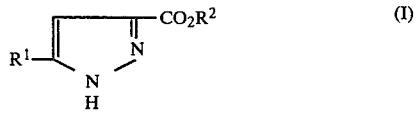

wherein $R^1$ represents an alkyl group of 7 to 11 carbon atoms and $R^2$ represents a hydrogen atom or a lower alkyl group.

Although the derivative of pyrazole represented by the above-mentioned general formula (I) includes publicly known compounds (refer to Keskin et al., Istanbul University, Fen. Fak. Mecum. Setic., 34,95–108, 1969), concerning the pharmacological properties of the above-mentioned derivatives of pyrazole, nothing has been reported.

The derivatives of pyrazole represented by the abovementioned general formula (I) (hereinafter referred to as the present compounds) are possibly synthesized by the following method:

Sodium enolate represented by the general formula (II):

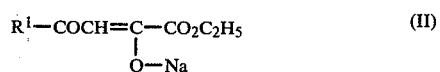

wherein $R^1$ means the same as mentioned above, respectively, which is obtainable by the Claisen's condensation of higher-alkyl methyl ketone and diethyl oxalate is heated in a mineral acid together with hydrazine hydrate under reflux for 4 to 10 hours with stirring to obtain ethyl ester of 5-alkylpyrazole carboxylic acid.

In the next step, the thus obtained ester is brought into reaction with sodium hydroxide in an aqueous lower alcoholic solution at about 100° C. to obtain 5-alkylpyrazole-3-carboxylic acid corresponding to the above-mentioned ester. In addition, by heating the above-mentioned sodium enolate together with hydrazine sulfate in an aqueous lower alcoholic solution of sodium hydroxide under reflux for 2 to 3 hours, 5-alkylpyrazole-3-carboxylic acids are also obtained.

The concrete method for synthesizing each of the present compounds and their physical- and chemical properties are shown in Examples 1 to 6 described later.

The toxicological and pharmacological properties of the present compounds are described as follows:

1. Toxicological property

Test method for acute toxicity:

Male ICR mice of body weight of 21 to 25 g were divided into several groups consisting of 8 animals and were fasted for 17 to 18 hours and then given orally each of the present compounds or nicotinic acid dissolved or dispersed in an aqueous 1% CMC soluion at a rate of 0.2 ml/10 g body weight. The administered levels of each of the present compound were 2.5 g/kg body weight and 5.0 g/kg, and from the mortalities at both levels, $LD_{50}$ was roughly calculated and compared with $LD_{50}$ of nicotinic acid.

The results showed that each of the present compounds had a $LD_{50}$ value over 5.0 g/kg body weight which was much larger than that of nicotinic acid, 4.5 g/kg.

2. Pharmacological property

Pharmacological tests were carried out on each of the present compounds while using nicotinic acid as a reference.

(i) Pharmacological test against hypertriglyceridemia:

Seven groups of male SD rats each weighing 232–237 g, each group consisting of 6 animals, were used for the test animals and one group consisting of 12 animals was used as control. The groups were made to be hypertriglyceridemia by giving an aqueous 10% by weight solution of fructose for 2 days, those of control group being given tap water. The administration of six kinds of the present derivatives and of nicotinic acid was as follows:

Each specimen of the present pyrazole derivatives and nicotinic acid was dissolved or dispersed into an aqueous 1% solution of carboxymethylcellulose (CMC) at a predetermined concentration, and the thus prepared solution or dispersion was orally administered 3 times in the volume of 0.5 ml/100 g body weight, that is, first dose just after the commencement of the present test, second dose after 24 hours of the first administration and third dose after 18 hours of the second administration. The dose of each compound was set so that each animal intaked 300 mg/kg of each compound as free carboxylic acid. The rats of control group were given the aqueous 1% solution of CMC only three times at the same intervals as the test groups. All the groups were fed with the same diet during the test period.

After 48 hours of the commencement of the test, blood sample was collected from each animal by amputation of the carotid artery, and serum was separated from the blood sample and frozen to be kept until lipid analysis.

Lipid analysis:

Serum triglyceride was determined by Acetylacetone Method, and the reduction percentage of lipid was calculated by the following formula:

$$\left(1 - \frac{\text{amount of triglyceride in serum of test animal}}{\text{amount of triglyceride in serum of control}}\right) \times 100 = \text{the reduction percentage of lipid}$$

wherein the amount is the average of the group.

Analysis for serum cholesterol:

The content of serum cholesterol was determined by an enzymatic method using cholesteroloxidase, and the reduction percentage of cholesterol was calculated by the following formula:

$$\left(1 - \frac{\text{amount of cholesterol in serum of test animal}}{\text{amount of cholesterol in serum of control}}\right) \times 100 = \text{the reduction percentage of cholesterol}$$

The results of the analyses are shown in Table 1.

TABLE 1

| Compound tested | Total Dose (mg/kg) | Reduction Percentage Triglyceride (%) | Reduction Percentage Cholesterol (%) |
| --- | --- | --- | --- |
| Ethyl 5-n-heptylpyrazole-3-carboxylate | 340 | 41.1 | 2.1 |
| Ethyl 5-n-nonylpyrazole-3-carboxylate | 335 | 63.1 | 29.5 |
| Ethyl 5-n-undecylpyrazole-3-carboxylate | 331 | 83.7 | 53.1 |
| 5-n-heptylpyrazole-3-carboxylic acid | 300 | 40.6 | 12.5 |
| 5-n-nonylpyrazole-3-carboxylic acid | 300 | 66.5 | 12.2 |
| 5-n-undecylpyrazole-3-carboxylic acid | 300 | 69.1 | 40.0 |
| nicotinic acid | 300 | 24.1 | 16.4 |

(ii) Pharmacological test against hypercholesterolemia:

Three groups of male SD rats each weighing ca. 150 g, each group consisting of five rats were used as the test animals and one group consisting of 10 rats was used as control. All animals were fed a high cholesterol diet consisted of 1% cholesterol, 0.2% sodium cholate, 5% olive oil and commercial diet up to total 100% for 7 days. The test compounds of the present invention and clofibrate, as a medicine for comparison, were respectively dissolved or dispersed in an aqueous 1% solution of CMC so that the volume of the solution or dispersion administered to each animal was 0.5 ml/100 g body weight/time, and the solution or dispersion was orally administered so that the amount of administration of each of the present pyrazole derivative or clofibrate was 200 mg/kg body weight/time. Actually, the administration was carried out once a day for 7 consecutive days. Water was taken ad lib. After 20 hours of fasting from the last administration, blood sample was taken by amputation of the carotid artery and the serum separated was frozen until the analysis of cholesterol shown as follows:

Cholesterol analysis

The content of serum cholesterol was determined by the above-mentioned method. The beta-lipoprotein-cholesterol was determined by "heparin-calcium precipitation method". The reduction percentages of cholesterol in serum and beta-lipoprotein were calculated in the same manner as above. The results are shown in Table 2.

TABLE 2

| Compound tested | Dose (mg/kg/day) | Reduction Percentage Cholesterol in serum | Reduction Percentage Cholesterol in beta-lipoprotein |
| --- | --- | --- | --- |
| 5-n-Nonylpyrazole-3-carboxylic acid | 200 | 11.1 | 0.6 |
| 5-n-Undecylpyrazole-3-carboxylic acid | 200 | 22.8 | 20.1 |
| Clofibrate (for comparison) | 200 | −3.5 | −2.0 |

As is seen in Tables 1 and 2, the present pyrazole derivatives have an excellent antilipemic activity in common superior to that of clofibrate which have been used as antilipemic agents for a long time.

The following description is the explanation of formulating the present pyrazole derivative into a pharmaceutical composition. In general, the present pyrazole derivative can be formulated into a pharmaceutical composition of dose unit form by the publicly known techniques. Since the present pyrazole derivative is generally administered via oral route, it is preferably formulated into tablets or capsulated form. For formulating the present pyrazole derivative into the dose unit form, vehicles, disintegrating agents, binding agents and lubricating agents which are used widely in pharmaceutical field may be actually usefull.

The dose level of the present pyrazole derivative naturally depends upon the degree of hyperlipemia, but, in general, the daily dose is 0.2 to 3.0 g/60 kg of body weight, preferably 0.5 to 1.5 g/60 kg body weight.

The following is the more detailed explanation of the synthesis and the formulation of the present pyrazole derivative while referring to non-limitative examples:

EXAMPLE 1

Synthesis of ethyl 5-n-heptylpyrazole-3-carboxylate:

In 500 ml of absolute ethanol, 12.6 g (0.55 mol) of metallic sodium was added slowly to dissolve it completely under agitation, and after cooling, a mixed liquid of 78 g (0.55 mol) of methyl n-heptyl ketone and 80.3 g (0.55 mol) of diethyl oxalate was slowly dropped into the above-mentioned solution at room temperature under agitation. The stirring was continued for 8 hours after the addition, at room temperature. Then, the deposited yellow precipitate was collected by filtration and recrystallized from ethanol to obtain sodium 1-ethoxycarbonyl-3-oxo-1-decenolate as pale yellow needle-like crystals amounting to 117 g which corresponds to the yield of 80.0%. After dissolving 26.4 g (0.10 mol) of the thus prepared sodium decenolate into 23 ml of glacial acetic acid, 5.5 g (0.11 mol) of hydrazine hydrate was dropped slowly into the solution under ice cooling. After the addition of hydrazine hydrate, the mixture was heated under reflux for 8 hours. Then, the reaction mixture was cooled and poured into iced water, and then neutralized with an aqueous saturated solution of sodium hydrogen carbonate and extracted with benzene. The benzene layer was washed with an aqueous saturated solution of sodium chloride and dried over anhydrous sodium sulfate. After distilling off the solvent under a reduced pressure, the residue was recrystallized from petroleum ether to obtain the object as colourless prisms amounting to 11.5 g which corresponds to the yield of 54.8% theoretical.

Elementary analysis: found: 65.58% of C, 9.35% of H and 11.60% of N calcd. for $C_{13}H_{22}O_2N_2$: 65.51% of C, 9.31% of H and 11.76% of N.

Infrared absorption spectrum $\nu_{max}^{nujol}$ 3300 to 3100 cm$^{-1}$ ($\nu_{NH}$) and 1718 cm$^{-1}$ ($\nu_{C=O}$).

Mass spectrum, m/e: 238 (M+).

Nuclear magnetic resonance spectrum (NMR) (in CDCl$_3$)δ:

0.85 (3H, t, J=6 Hz, $\underline{CH_3}(CH_2)_6$) 1.2 to 1.5 (11H, $CH_3\underline{(CH_2)_4}(CH_2)_2$ and $\underline{CH_3}CH_2OCO$) 1.65 (2H, m, $CH_3(\overline{CH_2})_4-\underline{CH_2}-CH_2$)

2.72 (2H, t, J=8 Hz, $CH_3(CH_2)_5-\underline{CH_2}$) 4.35 (2H, q, J=7 Hz, $CH_3-\underline{CH_2}-OCO$) 6.55 (1H, s, H in the pyrazole ring) 11.30 (1H, br., NH which disappears by treatment with D$_2$O)

EXAMPLE 2

Synthesis of 5-n-heptylpyrazole-3-carboxylic acid:

Into 81 ml of a 5% methanolic solution of sodium hydroxide, 20.0 g (0.084 mol) of ethyl 5-n-heptylpyrazole-3-carboxylate obtained in Example 1 was dissolved, and the solution was heated for 5 hours under a reflux condenser. After cooling the reaction mixture water was added, then methanol was distilled off under a reduced pressure, and the residue was acidified (pH of about 2) with concentrated hydrochloric acid. The deposited white precipitate was collected by filtration and recrystallized from a mixture of distilled water and methanol to obtain the object, 5-n-heptylpyrazole-3-carboxylic acid, as colourless needle-like crystals melting at 169°–171° C. in an amount of 13.3 g corresponding to the yield of 75.2%.

Elementary analysis: found: 62.71% of C, 8.50% of H and 13.42% of N; calcd. as $C_{11}H_{18}O_2N_2$: 62.83% of C, 8.63% of H and 13.32% of N.

Infrared absorption spectrum $\nu_{max}^{KBr}$ 3240 cm$^{-1}$ (br. $\nu_{OH\ and\ NH}$), 3000 to 2300 cm$^{-1}$ (br. $\nu_{NH_2+CO_2H}$) and 1700 cm$^{-1}$ ($\nu_{C=O}$).

Mass spectrum m/e: 210 (M+).

NMR (in d$_6$-DMSO)δ:

0.87 (3H, t, J=7 Hz, $\underline{CH_3}(CH_2)_6$) 1.2 to 1.5 (8H, br. s, $CH_3-\underline{(CH_2)_4}-CH_2CH_2$) 1.65 (2H, m, $CH_3(\overline{CH_2})_4-\underline{CH_2}-CH_2$) 2.61 (2H, t, J=7 Hz, $CH_3(CH_2)_4-\overline{CH_2}-\underline{CH_2}$) 6.52 (1H, s, H in the pyrazole ring) 10.65 (2H, br., NH and CO$_2$H which disappear by treatment with D$_2$O).

EXAMPLE 3

Synthesis of ethyl 5-n-nonylpyrazole-3-carboxylate:

After slowly adding and dissolving 5.2 g (0.23 mol) of metallic sodium into 300 ml of absolute ethanol under agitation, the clear solution was cooled and a liquid mixture of 39 g (0.23 mol) of methyl n-nonyl ketone and 33.6 g (0.23 mol) of diethyl oxalate was dropped slowly into the above-mentioned solution at room temperature under agitation. After the addition was over, the reaction mixture was heated at 60° C. under agitation for 5 hours. Then, the reaction mixture was cooled with iced water, and the deposited yellow precipitate was collected by filtration and recrystallized from ethanol to obtain sodium 1-ethoxycarbonyl-3-oxo-1-dodecenolate as pale yellow needle-like crystals in an amount of 44 g corresponding to the yield of 65.5%.

In 23 ml of glacial acetic acid, 26.0 g (0.09 mol) of the thus obtained dodecenolate was dissolved, and 5.0 g (0.10 mol) of hydrazine hydrate was slowly dropped into the solution with ice cooling and stirring. After the addition, the reaction mixture was heated under reflux for 6 hours. Then, the reaction mixture was cooled and poured into iced water, and was neutralized with a saturated aqueous solution of sodium hydrogen carbonate and extracted with benzene. The benzene layer was isolated, washed with a saturated aqueous solution of sodium chloride and dried with anhydrous sodium sulfate. Then, the dried benzene layer was subjected to distillation under a reduced pressure to remove the solvent, and the residue was recrystallized from n-hexane to obtain the object, ethyl 5-n-nonylpyrazole-3-carboxylate as colourless needle-like crystals melting at 37° to 38° C. in an amount of 14.5 g corresponding to the yield of 63.4%.

Elementary analysis: found: 67.92% of C, 9.80% of H and 10.88% of N; Calcd. as $C_{15}H_{26}O_2N_2$: 67.63% of C, 9.84% of H and 10.52% of N.

Infrared absorption spectrum $\nu_{max}^{nujol}$ 3300 to 3100 cm$^{-1}$ ($\nu_{NH}$) and 1720 cm$^{-1}$ ($\nu_{C=O}$).

Mass spectrum, m/e: 266 (M+).

NMR (in CDCl$_3$)δ:

0.85 (3H, t, J=6 Hz, $\underline{CH_3}(CH_2)_8$) 1.2 to 1.5 (15H, $CH_3\underline{(CH_2)_6}-CH_2CH_2$ and $\underline{CH_3}CH_2OCO$) 1.65 (2H, m, $CH_3(\overline{CH_2})_6-\underline{CH_2}-CH_2$) 2.72 (2H, t, J=8 Hz, $CH_2(CH_2)_7-\underline{CH_2}$) 4.37 (2H, q, J=7 Hz, $CH_3-\underline{CH_2}-OCO$) 6.60 (1H, s, H in the pyrazole ring)

12.47 (1H, br., NH which disappears by treatment with D$_2$O).

EXAMPLE 4

Synthesis of 5-n-nonylpyrazole-3-carboxylic acid:

In the same manner as in Example 2, 12.0 g (0.045 mol) of ethyl 5-n-nonylpyrazole-3-carboxylate obtained in Example 3 was hydrolized to 5-n-nonylpyrazole-3-carboxylic acid, which was recrystallized from a mixture of acetone and ethanol to obtain colourless needle-like crystals melting at 147° to 149° C. in an amount of 7.2 g corresponding to the yield of 67.3%.

Elementary analysis:

found: 65.60% of C, 9.23% of H and 11.82% of N; calcd. as $C_{13}H_{22}O_2N_2$: 65.51% of C, 9.31% of H and 11.76% of N.

Infrared absorption spectrum $\nu_{max}^{KBr}$ 3280 cm$^{-1}$ (br. $\nu_{OH}$), 3000 to 2300 cm$^{-1}$ (br. $\nu_{NH_2+}$) and 1680 cm$^{-1}$ ($\nu_{C=O}$).

Mass spectrum: m/e 238 (M+).
NMR (in d$_6$-DMSO)δ:
0.85 (3H, t, J=7 Hz, CH$_3$(CH$_2$)$_8$) 1.2 to 1.5 (12H, br. s, CH$_3$(CH$_2$)$_6$—CH$_2$CH$_2$) 1.65 (2H, m, CH$_3$(CH$_2$)$_6$—CH$_2$—CH$_2$) 2.61 (2H, t, J=7 Hz, CH$_3$(CH$_2$)$_6$—CH$_2$—CH$_2$) 6.45 (1H, s, H in the pyrazole ring) 7.87 (2H, br. NH and CO$_2$H which disappear by treatment with D$_2$O).

EXAMPLE 5:

Synthesis of ethyl 5-n-undecylpyrazole-3-carboxylate:

In the same manner as in Example 3, 74 g of sodium 1-ethoxycarbonyl-3-oxo-1-tetradecenolate was obtained from 5.8 g (0.25 mol) of metallic sodium, 50 g (0.25 mol) of methyl n-undecyl ketone and 36.5 g (0.25 mol of diethyl oxalate. Then, in the same manner as in Example 3, 37 g (0.11 mol) of the thus obtained sodium tetradecenolate was brought into reaction with 6.5 g (0.13 mol) of hydrazine hydrate to obtain the crude ethyl 5-n-undecylpyrazole-3-carboxylate, which was recrystallized from n-hexane to obtain colourless needle-like crystals melting at 39° to 40° C. in an amount of 24.2 g corresponding to the yield of 71.0%.

Elementary analysis: found: 67.36% of C, 9.85% of H and 10.79% of N; calcd. as C$_{17}$H$_{30}$O$_2$N$_2$: 67.63% of C, 9.84% of H and 10.52% of N.

Infrared absorption spectrum
$\nu_{max}^{nujol}$ 3200 to 3100 cm$^{-1}$ ($\nu_{NH}$) and 1722 cm$^{-1}$ ($\nu_{C=O}$).

Mass spectrum: m/e 294 (M+).
NMR (in CDCl$_3$)δ:
0.90 (3H, t, J=6 Hz, CH$_3$(CH$_2$)$_{10}$) 1.2 to 1.6 (19H, CH$_3$(CH$_2$)$_8$(CH$_2$)$_2$ and CH$_3$CH$_2$OCO) 1.7 (2H, m, CH$_3$(CH$_2$)$_8$—CH$_2$—CH$_2$) 2.88 (2H, t, J=8 Hz, CH$_3$(CH$_2$)$_8$CH$_2$—CH$_2$) 4.65 (2H, q, J=7 Hz, CH$_3$—CH$_2$—OCO) 6.98 (1H, s, H in the pyrazole ring) 12.7 (1H, br., NH which disappears by treatment with D$_2$O).

EXAMPLE 6

Synthesis of 5-n-undecylpyrazole-3-carboxylic acid:

In the same manner as in Example 2, 10 g (0.03 mol) of ethyl 5-n-undecylpyrazole-3-carboxylate obtained in Example 5 was hydrolized to 5-n-undecylpyrazole-3-carboxylic acid, which was recrystallized from ethanol to obtain, colourless needle-like crystals melting at 151° to 153° C. in an amount of 7.8 g corresponding to the yield of 86.3%.

Elementary analysis: found: 67.36% of C, 9.85% of H and 10.79% of N; calcd. as C$_{15}$H$_{26}$O$_2$N$_2$: 67.63% of C, 9.84% of H and 10.52% of N.

Infrared absorption spectrum
$\nu_{max}^{KBr}$ 3270 cm$^{-1}$ (br. $\nu_{OH}$ and $\nu_{NH}$), 300 to 2300 cm$^{-1}$
(br. $\nu_{NH2+}$ $_{and\ CO2H}$) and 1710 cm$^{-1}$ ($\nu_{C=O}$).
Mass spectrum: m/e 266 (M+).
NMR (in d$_6$-DMSO)δ:
0.85 (3H, t, J=7 Hz, CH$_3$(CH$_2$)$_{10}$) 1.2 to 1.5 (16H, br. s, CH$_3$(CH$_2$)$_8$—CH$_2$CH$_2$) 1.60 (2H, m, CH$_3$(CH$_2$)$_8$—CH$_2$—CH$_2$) 2.55 (2H, t, J=7 Hz, CH$_3$(CH$_2$)$_8$CH$_2$—CH$_2$) 5.20 (2H, br. NH and CO$_2$H which disappear by treatment with D$_2$O)
6.31 (1H, s, H in the pyrazole ring).

EXAMPLE 7

Preparation of tablets containing the present compound:

After mixing 200 g of 5-n-heptylpyrazole-3-carboxylic acid, 50 g of lactose, 20 g of potato starch, 15 g of CMC and 10 g of methylcellulose uniformly, the mixture was shaped into particles by introducing the mixture together with an aqueous 50% ethanolic solution into a tumbling forming machine, and the thus obtained particles were dried by a fluidizing dryer. After drying, the particles were sifted by screening machine provided with a sieve of 32 mesh of Taylor standards. The particles passed through the mesh were mixed with 3 g of talc and 2 g of magnesium stearate and the mixture was pressed in a rotary tabletting machine into tablets of 9 mm in diameter and 300 mg in each weight.

EXAMPLE 8:

Preparation of capsulated composition of the present compound:

Particles were prepared in the same manner as in Example 7, however, using 5-n-nonylpyrazole-3-carboxylic acid instead of 5-n-heptylpyrazole-3-carboxylic acid in Example 7, and the particles were capsuled in No. 1 hard capsules by using a capsulating machine at a rate of 300 mg of the particles/capsule.

What is claimed is:
1. An antihyperlipemic composition in dosage form, which comprises an antihyperlipemically effective amount of a compound of the formula:

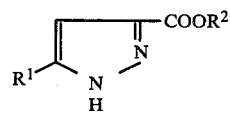

wherein R$^1$ represents an alkyl group of 7-11 carbon atoms and
R$^2$ represents H or a lower alkyl group of up to two carbon atoms, and a pharmaceutically acceptable carrier.

2. A pharmaceutical composition according to claim 1, wherein said 5-alkylpyrazole-3-carboxylic acid is 5-n-heptylpyrazole-3-carboxylic acid.

3. A pharmaceutical composition according to claim 1, wherein said 5-alkylpyrazole-3-carboxylic acid is 5-n-nonylpyrazole-3-carboxylic acid.

4. A pharmaceutical composition according to claim 1, wherein said 5-alkylpyrazole-3-carboxylic acid is 5-n-undecylpyrazole-3-carboxylic acid.

5. A pharmaceutical composition according to claim 1, wherein said ester of 5-alkylpyrazole-3-carboxylic acid is ethyl 5-n-heptylpyrazole-3-carboxylate.

6. A pharmaceutical composition according to claim 1, wherein said ester of 5-alkylpyrazole-3-carboxylic acid is ethyl 5-n-nonylpyrazole-3-carboxylate.

7. A pharmaceutical composition according to claim 1, wherein said ester of 5-alkylpyrazole-3-carboxylic acid is ethyl 5-n-undecylpyrazole-3-carboxylate.

8. A method for the treatment of hyperlipemia which comprises administering to the patient suffering from hyperlipemia an antihyperlipemically effective amount of a compound of the formula:

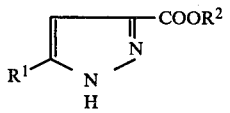

wherein R$^1$ represents an alkyl group of 7-11 carbon atoms and
R$^2$ represents H or a lower alkyl group of up to two carbon atoms.

* * * * *